(12) United States Patent
Garnett et al.

(10) Patent No.: US 10,371,668 B2
(45) Date of Patent: Aug. 6, 2019

(54) APPARATUS AND METHODS FOR PROBING A MATERIAL AS A FUNCTION OF DEPTH USING DEPTH-DEPENDENT SECOND HARMONIC GENERATION

(71) Applicant: Vanderbilt University, Nashville, TN (US)

(72) Inventors: Joy Garnett, Nashville, TN (US); Halina Krzyzanowska, Nashville, TN (US); Norman H. Tolk, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 124 days.

(21) Appl. No.: 15/324,100

(22) PCT Filed: Jul. 13, 2015

(86) PCT No.: PCT/US2015/040158
§ 371 (c)(1),
(2) Date: Jan. 5, 2017

(87) PCT Pub. No.: WO2016/007950
PCT Pub. Date: Jan. 14, 2016

(65) Prior Publication Data
US 2017/0205377 A1  Jul. 20, 2017

Related U.S. Application Data

(60) Provisional application No. 62/023,378, filed on Jul. 11, 2014.

(51) Int. Cl.
*G01N 29/24* (2006.01)
*G01N 21/63* (2006.01)
(Continued)

(52) U.S. Cl.
CPC ....... *G01N 29/2418* (2013.01); *G01N 21/636* (2013.01); *G01N 21/8422* (2013.01);
(Continued)

(58) Field of Classification Search
CPC ............ G01N 21/636; G01N 21/1717; G01N 2021/637–638; G01N 2291/02827;
(Continued)

(56) References Cited

U.S. PATENT DOCUMENTS 4,211,488 A * 7/1980 Kleinknecht ........ G01N 21/314
250/559.16
4,710,030 A * 12/1987 Tauc ................... G01N 21/1702
356/432

(Continued)

OTHER PUBLICATIONS

Ok et al, Bulk characterization methods for non-centrosymmetric materials: secondharmonic generation, piezoelectricity, pyroelectricity, and ferroelectricity, Chem. Soc. Rev., 2006, 35, 710-717 (Year: 2006).*

(Continued)

*Primary Examiner* — Justin Seo
*Assistant Examiner* — David L Singer
(74) *Attorney, Agent, or Firm* — Locke Lord LLP; Tim Tingkang Xia, Esq.

(57) ABSTRACT

A method for non-invasively probing at least one physics property of a solid material. In one embodiment, the method has the steps of splitting a photon beam into a first photon beam and a second photon beam, exposing the solid material to the first photon beam to generate a coherent acoustic phonon wave in the solid material at time t, and exposing the solid material to the second photon beam at a time t+Δt, where t+Δt≥t, to generate corresponding second harmonic generation signals, where from the corresponding second
(Continued)

harmonic generation signals, the at least one physics property of the solid material is determinable.

37 Claims, 7 Drawing Sheets

(51) Int. Cl.
*G01N 29/04* (2006.01)
*G01N 29/44* (2006.01)
*G01N 21/84* (2006.01)
*G01N 21/95* (2006.01)

(52) U.S. Cl.
CPC ....... *G01N 21/9505* (2013.01); *G01N 29/043* (2013.01); *G01N 29/4454* (2013.01); *G01N 2021/8438* (2013.01); *G01N 2021/8477* (2013.01)

(58) Field of Classification Search
CPC ... G01N 2291/0427; G01N 2291/1706; G01B 11/0666
See application file for complete search history.

(56) References Cited

U.S. PATENT DOCUMENTS

| | | | | |
|---|---|---|---|---|
| 5,270,797 | A * | 12/1993 | Pollak | G01N 21/1717 356/417 |
| 5,633,711 | A * | 5/1997 | Nelson | G01B 11/0666 356/318 |
| 5,706,094 | A * | 1/1998 | Maris | G01N 21/1717 356/432 |
| 5,748,317 | A * | 5/1998 | Maris | G01N 21/171 356/502 |
| 5,748,318 | A * | 5/1998 | Maris | G01N 21/1702 356/630 |
| 5,844,684 | A * | 12/1998 | Maris | G01N 21/1717 356/432 |
| 6,008,906 | A * | 12/1999 | Maris | G01N 21/1717 250/226 |
| 6,025,918 | A * | 2/2000 | Maris | G01N 21/1717 356/388 |
| 6,038,026 | A * | 3/2000 | Maris | G01B 11/303 356/514 |
| 6,047,011 | A | 4/2000 | Cook | |
| 6,201,601 | B1 * | 3/2001 | Vaez-Iravani | G01J 3/44 356/237.4 |
| 6,256,100 | B1 * | 7/2001 | Banet | G01B 11/0666 356/432 |
| 7,006,221 | B2 * | 2/2006 | Wolf | G01B 11/0666 356/369 |
| 8,537,363 | B2 * | 9/2013 | Maris | G01N 21/1717 356/445 |
| 8,643,833 | B1 * | 2/2014 | Hung | G01N 21/9501 356/237.1 |
| 2001/0028460 | A1 * | 10/2001 | Maris | G01N 21/1702 356/432 |
| 2002/0054295 | A1 * | 5/2002 | Maris | G01N 21/8422 356/496 |
| 2002/0135784 | A1 * | 9/2002 | Morath | G01B 11/0666 356/630 |
| 2003/0206292 | A1 * | 11/2003 | Some | G01N 21/171 356/237.1 |
| 2006/0044641 | A1 * | 3/2006 | Alles | G01N 21/63 359/328 |
| 2006/0272418 | A1 * | 12/2006 | Maris | A61B 5/0097 73/606 |
| 2006/0272419 | A1 * | 12/2006 | Maris | A61B 5/0097 73/606 |
| 2011/0206075 | A1 | 8/2011 | Ji et al. | |
| 2014/0027808 | A1 | 1/2014 | Ni et al. | |

OTHER PUBLICATIONS

Park, Dissertation: Second Harmonic Generation in Si/SiO2 Systems, Vanderbilt University, Aug. 2010 (Year: 2010).*
Corn et al, Optical Second Harmonic Generation as a Probe of Surface Chemistry, Chem. Rev. 1994, 94, 107-125 (Year: 1994).*
Matsuda, Coherent Shear Phonon Generation and Detection with Ultrashort Optical Pulses, The American Physical Society vol. 93, No. 9 week ending Aug. 27, 2004 (Year: 2004).*
Glinka et al, Spatially resolved pump-probe second harmonic generation study of multilayer semiconductor heterostructures, Appl. Phys. Lett. 91, 231104 (2007) (Year: 2007).*
NDT Resource Center, Wave Propagation, (Year: 2003).*
Korean Intellectual Property Office (ISR/KR), "International Search Report for PCT/US2015/040158", Korea, dated Oct. 22, 2015.
T. Saka et al. Y, Strain of GaAs/GaAsP Superlattices Used as Spin-Polarized Electron Photocathodes, Determined by X-Ray Diffraction, Surf. Sci. and Nanotech. 8 (2010) 125.
X. Jin et al. High-Performance Spin-Polarized Photocathodes Using a GaAs/GaAsP Strain-Compensated Superlattice, Appl. Phys. Express 6 (2013) 015801.
C. Schriever et al. Strained silicon Photonics, Materials 5 (2012) 889.
Ji-Hong Zhao et al. Enhancement of second-harmonic generation from silicon stripes under external cylindrical strain, Opt. Lett. 34 (2009) 3340.
M. M. Roberts et al. Elastically relaxed free-standing strained-silicon nanomembranes, Nature Mat. 5 (2006) 388.
M.K. Vanbel et al. Electric-Field-Induced Second-Harmonic Generation Demonstrates Different Interface Properties of Molecular Beam Epitaxy Grown MgO on Si, J. Phys. Chem. C, 118 (2014) 1919.
I. L. Lyubchanskii et al. Second-harmonic generation from realistic film-substrate interfaces: The effects of strain, Appl. Phys. Lett. 76 (2000) 1848.
C. Thomsen et al., Surface Generation and Detection of Phonons by Picosecond Light Pulses, Phys. Rev. B 34 (1986) 4129.
Yu.D. Glinka et al. Ultrafast dynamics of interfacial electric fields in semiconductor hetero-structures monitored by pump-probe second-harmonic generation, Appl. Phys. Lett. 81 (2002) 3717.
H. Park, et al. Applied Physics Letters 95 (2009) 062102.
H. Park et al. Polarization-dependent temporal behavior of second harmonic generation in Si/SiO2 systems, J. Opt. 13 (2011) 055202.
C. Thomsen et al., Coherent Phonon Generation and Detection by Picosecond Light Pulses, Phys. Rev. Lett. 53 (1984) 989.
O. Matsuda et al. Coherent shear phonon generation and detection with picosecond laser acoustics, Phys. Rev. B 77 (2008)224110.

* cited by examiner

$0° \leq h < H_1 + H_2$ $0° \leq \alpha_1 < 90°$ $0° < \alpha_2 < 90°$

APPARATUS AND METHODS FOR PROBING A MATERIAL AS A FUNCTION OF DEPTH USING DEPTH-DEPENDENT SECOND HARMONIC GENERATION

CROSS-REFERENCE TO RELATED PATENT APPLICATION

This PCT application claims the benefit, pursuant to 35 U.S.C. § 119(e), of U.S. provisional patent application Ser. No. 62/023,378, filed Jul. 11, 2014, entitled "APPARATUS AND METHODS FOR PROBING A MATERIAL AS A FUNCTION OF DEPTH USING DEPTH-DEPENDENT SECOND HARMONIC GENERATION," by Joy Garnett et al., which is hereby incorporated herein by reference in its entirety. This application relates to U.S. Pat. No. 6,856,159, issued Feb. 15, 2005, entitled "CONTACTLESS OPTICAL PROBE FOR USE IN SEMICONDUCTOR PROCESSING METROLOGY," by Norman H. Tolk et al., which is hereby incorporated herein by reference in its entirety. This application also relates to U.S. Pat. No. 7,158,284, issued Jan. 2, 2007, entitled "APPARATUS AND METHODS OF USING SECOND HARMONIC GENERATION AS A NON-INVASIVE OPTICAL PROBE FOR INTERFACE PROPERTIES IN LAYERED STRUCTURES" by Alles et al., which is hereby incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [15] represents the first reference cited in the reference list, namely, C. Thomsen et al., *Coherent Phonon Generation and Detection by Picosecond Light Pulses*, Phys. Rev. Lett. 53 (1984) 989.

STATEMENT OF FEDERALLY-SPONSORED RESEARCH

This invention was made with government support under Contract No. DE-FG02-99ER45781 awarded by the Department of Energy and Contract No. W911NF-10-1-0363 awarded by the Army Research Office. The government has certain rights in the invention.

FIELD OF THE INVENTION

The present invention generally relates to the utilization of depth-dependent second harmonic generation as a non-invasive probe for at least one physics property of a material as a function of depth.

BACKGROUND OF THE INVENTION

There is at present no satisfactory nondestructive way to sensitively measure or characterize defects, strain and impurities as a function of depth with high resolution in solid materials including semiconducting and insulating materials. There is a great desire in the material science community to have this capability.

Therefore, a heretofore unaddressed need still exists in the art to address the aforementioned deficiencies and inadequacies.

SUMMARY OF THE INVENTION

The present invention, in one aspect, relates to a method for non-invasively probing at least one physics property of a solid material. In one embodiment, the solid material has a first surface, a second, opposite surface, and a body portion therebetween the first surface and the second surface, where a layered structure is formed with a transducing layer deposited on the solid material, and where as formed, the layered structure has a first surface that is a surface of the transducing layer, a second, opposite surface that is a surface of the solid material layer, and an interface therebetween.

In one embodiment, the method includes the steps of splitting a photon beam into a first photon beam and a second photon beam, and exposing the first surface of the layered structure to the first photon beam at time t with first incident angle $\alpha_1$ to induce a coherent acoustic phonon wave in the transducing layer, which travels into the body portion of the solid material layer with a moving surface.

The method further includes the step of exposing the first surface of the layered structure to the second photon beam at time t+Δt, where t+Δt≥t, with a second incident angle $\alpha_2$ to produce a first reflection beam and a second reflection beam, respectively, where the first reflection beam contains a first portion of the second photon beam that is reflected from the first surface of the layered structure, and the second reflection beam contains a second portion of the second photon beam that is reflected from the moving surface of the coherent acoustic phonon wave traveling in the body portion of the solid material layer at a depth h, causing an interference between the first reflection beam and the second reflection beam to generate corresponding second harmonic generation signals.

The method includes additional steps of detecting the second harmonic generation signals, measuring intensities of the second harmonic generation signals, and determining the at least one physics property of the solid material at or around the depth h from the measured second harmonic generation intensities.

In one embodiment, the incident photon beam includes substantially monochromatic electromagnetic radiation.

In one embodiment, the substantially monochromatic electromagnetic radiation is a laser beam such as a pulsed laser beam.

The at least one physics property of the solid material is at least one of defect, defect concentration, defect sensitivity, type of defect, spatial resolution, electronic structure, lattice, lattice mismatch, lattice disorder, dopants, impurities, interface(s), interfacial strain, interface roughness, interface state density, trapped charge density, surface recombination velocity, electrically active impurity, and interface morphology.

The present invention, in another aspect, relates to a method for non-invasively probing at least one physics property of a solid material, where the solid material has a first surface, a second, opposite surface, and a body portion therebetween the first surface and the second surface. In one embodiment, the method includes the steps of splitting a photon beam into a first photon beam and a second photon beam; with the first photon beam, generating a coherent acoustic phonon wave to travel in the body portion of the solid material with a moving surface at time t; and with the second photon beam, producing a first reflection beam and a second reflection beam, respectively, where the first reflection beam contains a first portion of the second photon beam that is not reflected from the coherent acoustic phonon wave, and the second reflection beam contains a second portion of the second photon beam that is reflected, at a time t+Δt, where t+Δt≥t, from the moving surface of the coherent acoustic phonon wave traveling in the body portion of the solid material layer at a depth h, causing an interference between the first reflection beam and the second reflection beam to generate corresponding second harmonic generation signals. The method further includes the step of measuring intensities of the corresponding second harmonic generation signals, from which the at least one physics property of the solid material at or around the depth h is determinable.

In yet another aspect, the present invention relates to a non-invasive optical probe for at least one physics property of a solid material, where the solid material has a first surface, a second, opposite surface, and a body portion therebetween the first surface and the second surface. In one embodiment, the probe has a light source for emitting a light beam, and optical means for splitting the light beam into a first photon beam to generate a coherent acoustic phonon wave to travel in the body portion of the solid material with a moving surface at time t, and a second photon beam to produce a first reflection beam and a second reflection beam, respectively, where the first reflection beam contains a first portion of the second photon beam that is not reflected from the coherent acoustic phonon wave, and the second reflection beam contains a second portion of the second photon beam that is reflected, at a time t+Δt, where t+Δt≥t, from the moving surface of the coherent acoustic phonon wave traveling in the body portion of the solid material layer at a depth h, causing an interference between the first reflection beam and the second reflection beam to generate corresponding second harmonic generation signals. The probe further has a detector for measuring intensities of the corresponding second harmonic generation signals, where the measured second harmonic generation signal intensities are associated with the at least one physics property of a solid material at or around the depth h.

In one embodiment, the light source is a laser.

The solid material is one of a semiconductor material, a metallic material, an insulator material, and a dielectric material. In one embodiment, the solid material is one of GaAs, GaSb, GaSb/GaAs, Si, $SiO_2$/Si and silicon on insulator (SOI).

In one embodiment, the optical means includes a splitter.

In one embodiment, the detector includes a photomultiplier tube.

In a further aspect, the present invention relates to a non-invasive optical probe for at least one physics property of a solid material, where the solid material has a first surface, a second, opposite surface, and a body portion therebetween the first surface and the second surface. In one embodiment, the probe has a laser source emitting a beam of pulses, where in operation the beam of pulses is split into a first photon beam to generate a coherent acoustic phonon wave to travel in the body portion of the solid material with a moving surface at time t, and a second photon beam to produce a first reflection beam and a second reflection beam, respectively, where the first reflection beam contains a first portion of the second photon beam that is not reflected from the coherent acoustic phonon wave, and the second reflection beam contains a second portion of the second photon beam that is reflected, at a time t+Δt, where t+Δt≥t, from the moving surface of the coherent acoustic phonon wave traveling in the body portion of the solid material at a depth h, causing an interference between the first reflection beam and the second reflection beam to generate corresponding second harmonic generation signals. The probe also has an optical system for measuring intensities of the corresponding second harmonic generation signals, wherein the measured second harmonic generation signal intensities are associated with the at least one physics property of the solid material at or around the depth h.

The present invention further relates to a method for non-invasively probing at least one physics property of a solid material. In one embodiment, such a method has the steps of splitting a photon beam into a first photon beam and a second photon beam, exposing the solid material to the first photon beam to generate a coherent acoustic phonon wave in the solid material at time t, and exposing the solid material to the second photon beam at a time t+Δt, where t+Δt≥t, to generate corresponding second harmonic generation signals, where from the corresponding second harmonic generation signals, the at least one physics property of the solid material is determinable.

The present invention in another aspect relates to a non-invasive probe for at least one physics property of a solid material. In one embodiment, such a probe has a photon source emitting a beam of pulses, where the beam of pulses in operation is split into a first photon beam to generate a coherent acoustic phonon wave in the solid material at time t, and a second photon beam to generate corresponding second harmonic generation signals. The probe further has an optical system for measuring the corresponding second harmonic generation signals, where from the measured corresponding second harmonic generation signals, the at least one physics property of the solid material is determinable.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

FIG. 2 illustrates (a) theoretical shape of a coherent acoustic pulse, where 2d defines the spatial size of the pulse and h represents elastic strain component [16]; and (b) a modification of crystal lattice due to transient strain caused by coherent acoustic phonon wave. The coherent pulses interact with the material firstly compress and subsequently tensile the crystal lattice, thereby providing additional, dynamic strain components to photo-elastic tensor according to one embodiment of the present invention.

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which has no influence on the scope of the invention. Additionally, some terms used in this specification are more specifically defined below.

Definitions

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing various embodiments of the invention and how to practice the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Overview of the Invention

The use of femtosecond laser pulses to characterize and control material properties at the quantum level has led to exciting developments at the frontier of condensed-matter physics. Particularly, recent advances in laser technology and nonlinear optics have opened up new venues for fundamental studies of electrical and physical properties of various electronic materials, including such materials having layered structures with interfaces therein. Among these approaches, second harmonic generation (hereinafter "SHG") analysis has several advantages. It has been known that the SHG, which is a direct measurement of second order non-linear susceptibility, $\chi^{(2)}$, is extremely sensitive to local electric and magnetic fields occurring at surfaces and at interfaces in layered structures. Unlike the electrical characterization methods, the SHG signal detects the electric and magnetic fields at interfaces of layered structures without directly contacting the surfaces of layered structures. Thus, the SHG can be used for in situ measurements. Additionally, the ability of an optical radiation to deeply penetrate into target materials may make the SHG a powerful probe for probing a material as a function of depth.

It is noted that use of elastic strain has been shown to influence and in many cases enhance, the optical and electronic performance of semiconductor based devices [1,2]. Electronically, the imposition of strain has been measured to increase electric mobility by 70% [3]. Optically, the presence of strain modifies the tensor elements of the second order optical nonlinear susceptibility, $\chi^{(2)}$, leading to significant enhancement of the SHG response in a single crystal [4].

Strain can be induced in semiconductor thin films with several different approaches [5, 6]. For examples, strain can be induced by ion implantation or during epitaxial fabrication using for example molecular beam epitaxy (hereinafter "MBE"). Externally imposed strain can be induced with an appropriate strain apparatus or with piezoelectric strain transducer. All of these strain methods have been shown to alter $\chi^{(2)}$ and consequently to enhance second harmonic generation. However, these methods have limitations. With ion implantation and MBE methods alone, the strain is fixed, permanent and varies depending on which complicated fabrication protocols are employed [7]. Conventional active methods, like external strain machines and traditional acoustics provide a changeable, transient strain that can work with various materials, but also have some limitations as well. External strain machines typically produce an inhomogeneous strain over a large area and cannot be incorporated directly into microelectronic or optoelectronic devices [8]. Traditional acoustic waves produce homogenous strain and can be incorporated directly into devices. However, the speeds at which these acoustic frequencies can be generated are limited to low GHz, which makes them too slow for ultrafast processes.

However, Applicants believe that there had been no application of the SHG to characterize physics properties as a function of depth in solid materials as disclosed by this disclosure.

In particular, this invention in one aspect relates to an innovative contactless, ultrafast pump-probe method, which involves a pump induced coherent acoustic soliton wave. This traveling wave provides a controllable, transient dynamic strain. A probe pulse arriving $\Delta t$ later results in a second-harmonic response, which is an extremely sensitive technique to detect changes in $\chi^{(2)}$ as a function of depth. It is noted that changes of $\chi^{(2)}$ can be caused by both inherent (caused by technological processes) and dynamic (caused by coherent acoustic solitons) strain in target materials such as AIII-BV (MBE-grown GaAs, GaSb/GaAs) and $SiO_2$/Si systems. Thus, from the measured corresponding SHG signals, one may elucidate inherent and dynamic strain mechanisms at the semiconductor/semiconductor and insulator/semiconductor interfaces as well as the bodies of the target materials with various lattice mismatches and film thicknesses, which are useful for evaluation and development of novel electronic devices (detectors and transistors) based on transient dynamic strain caused by the coherent acoustic solitons. It is noted that frequencies obtainable with acoustic solitons are on the order of 10's of GHz to low THz. In practicing the present invention, acoustic waves in the frequency regime of 60-100 GHz for excitation wavelengths from 780 to 890 nm and from 390 to 445 nm are achieved and utilized.

This novel and inventive depth-dependent characterization technique can, among other things, accurately examine order/disorder effect (produced by defects, dopants, dynamic strain, etc.) versus depth. Using the SHG, applicants are able to extract elements of the photoelastic and strain tensors under transient elastic strain and their respective effect on the target material's electronic structure. This technique has a spatial resolution on the order of tens of nanometers, is noninvasive and nondestructive, and is conducive to integration into fabrication processes. This novel and inventive technique is particularly useful in thin film growth processes and the determination of the quality of material structures used in optoelectronic industry, where lateral dimensions are on the order of microns, but depth dimensions are on the order of tens of nanometers.

Figure 1:
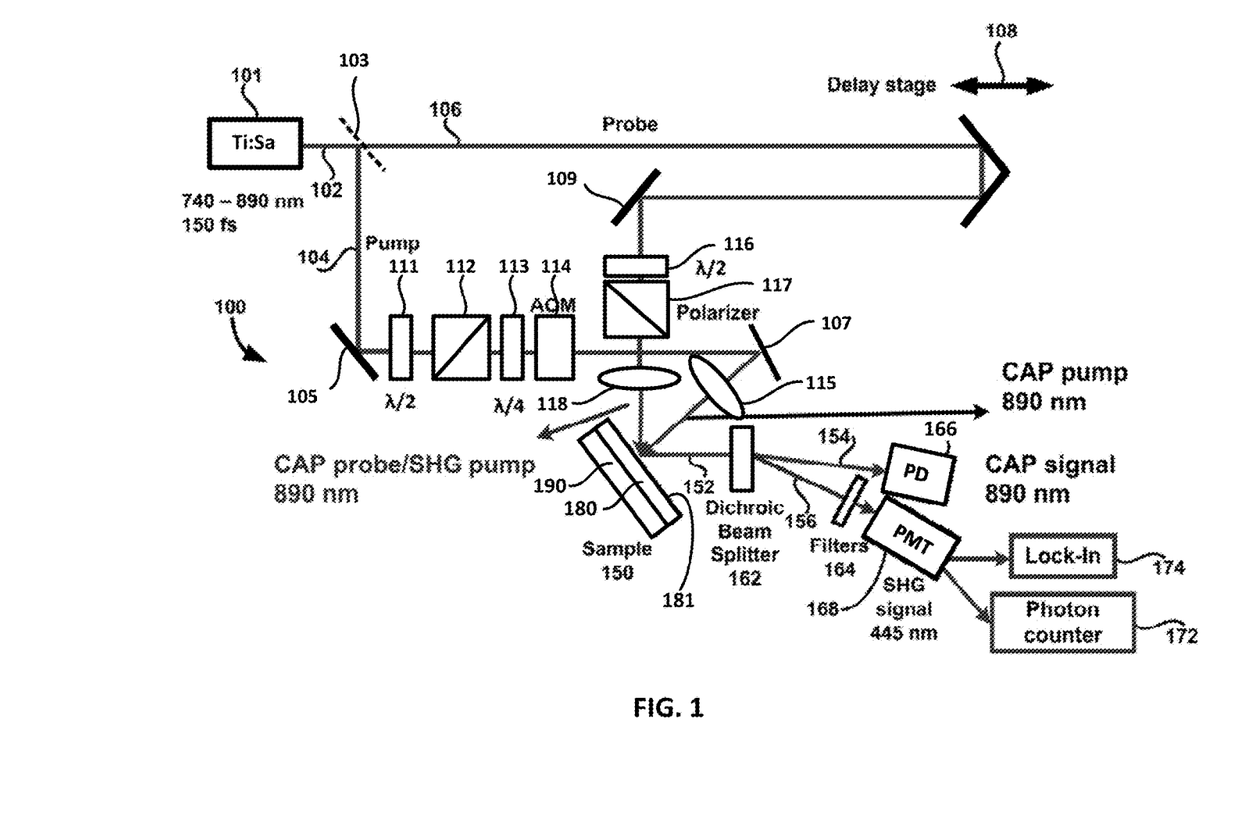
FIG. 1 schematically illustrates in part an optical probe for measuring physics properties in a solid material as a function of depth using depth-dependent second harmonic generation (SHG) according to one embodiment of the present invention, where AOM stands for acousto-optic modulator, λ/2, λ/4 stand for half and quarter wave plate, respectively, PD stands for photo detector, and PMT stands for photo-multiplier.
Figure 3:
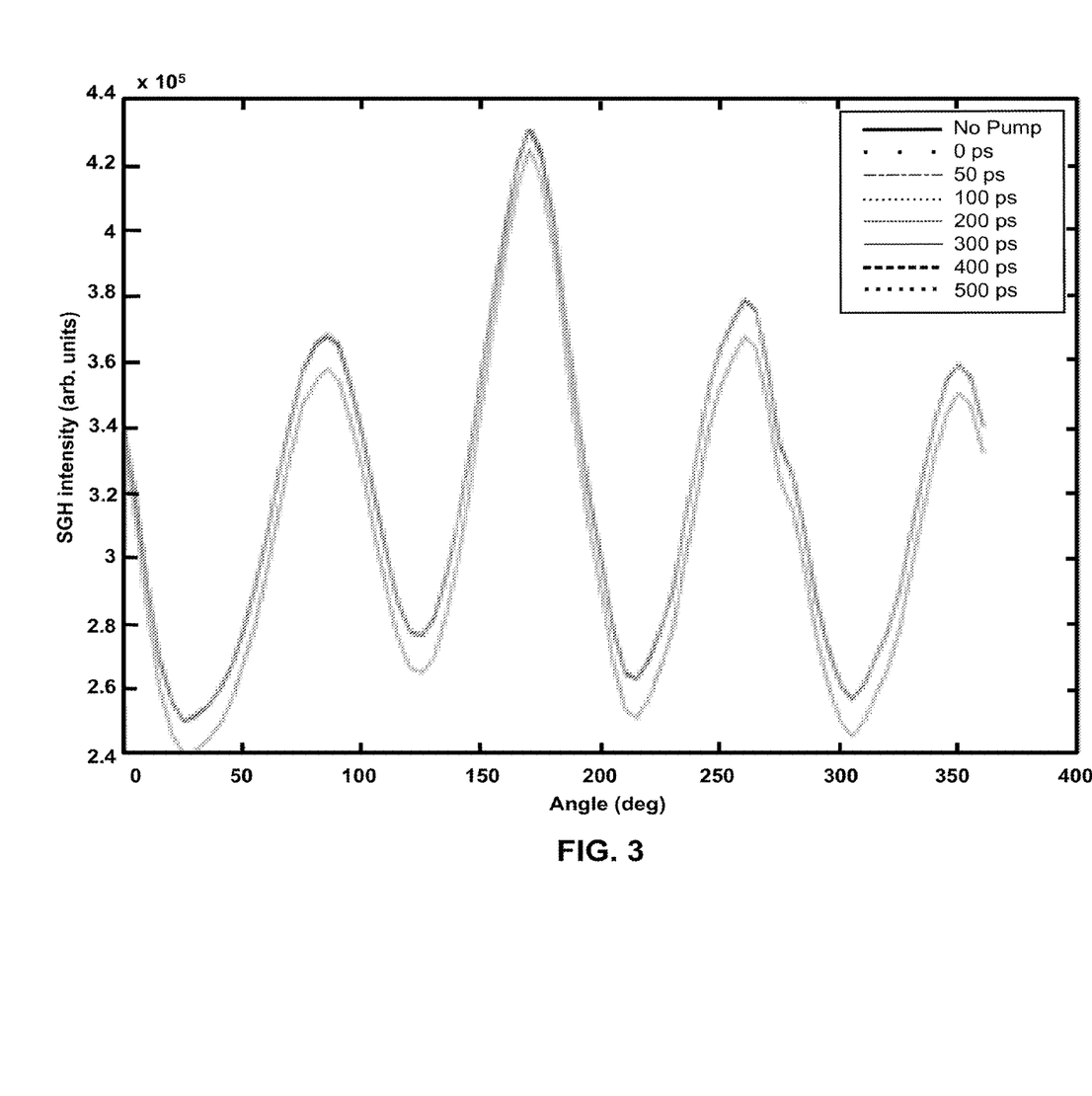
FIG. 3 illustrates a fourfold symmetry SHG diagrams collected by a PMT and photon counter system containing the total second harmonic response from the sample according to one embodiment of the present invention.
Figure 4:
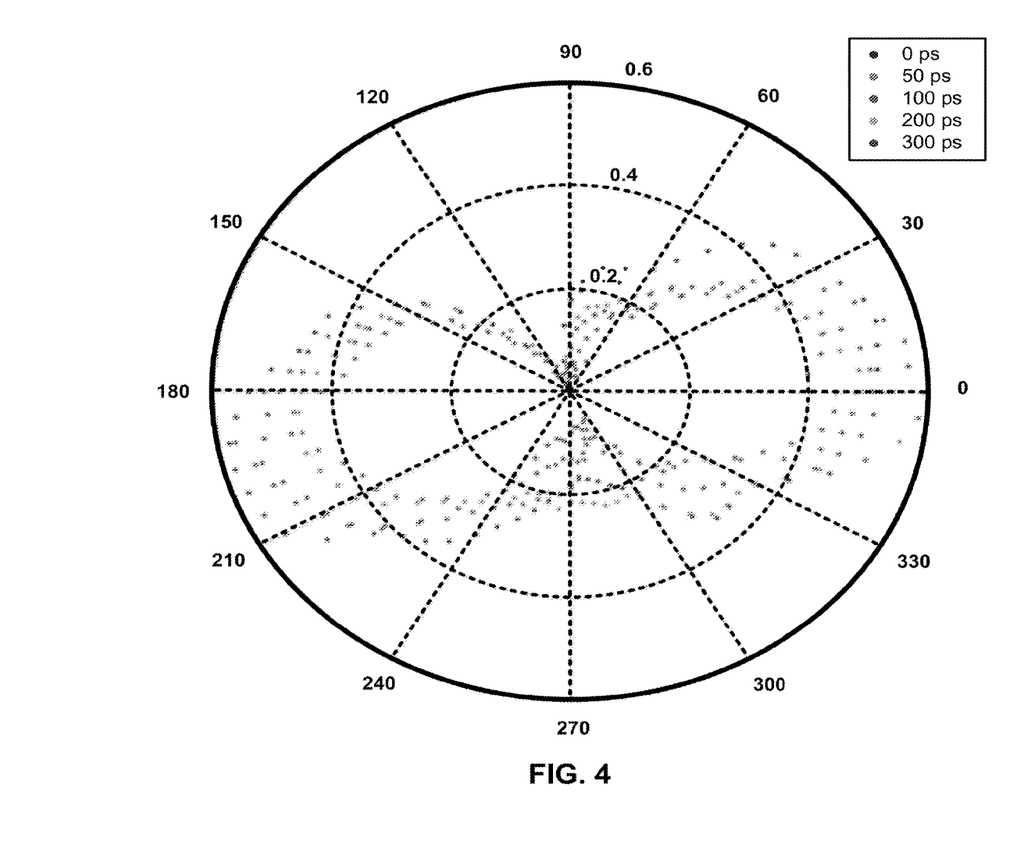
FIG. 4 illustrates a twofold symmetry SHG polar diagrams collected by PMT 168 and Lock-In 174 containing only second harmonic response from CAP transient strain according to one embodiment of the present invention.
Figure 5:
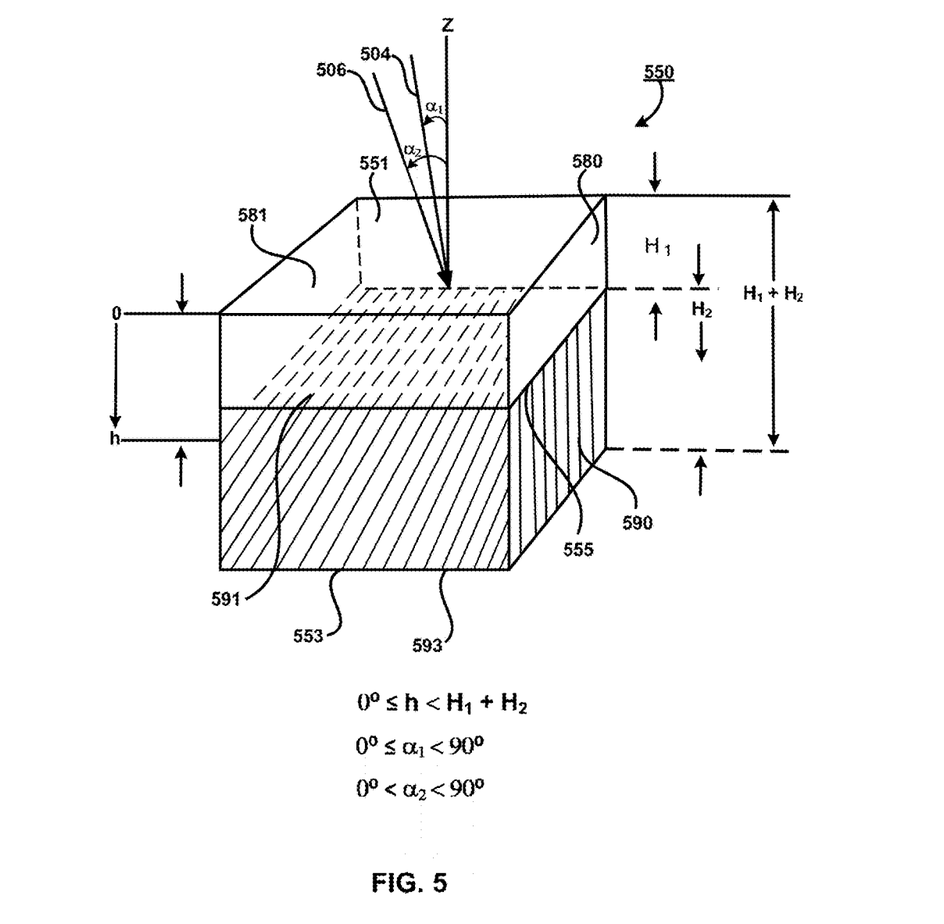
FIG. 5 shows schematically in part a non-invasively optical probe for at least one physics property of a solid material according to one embodiment of the present invention corresponding to a layered structure having one interface between a transducing layer and a solid material layer.
Figure 6:
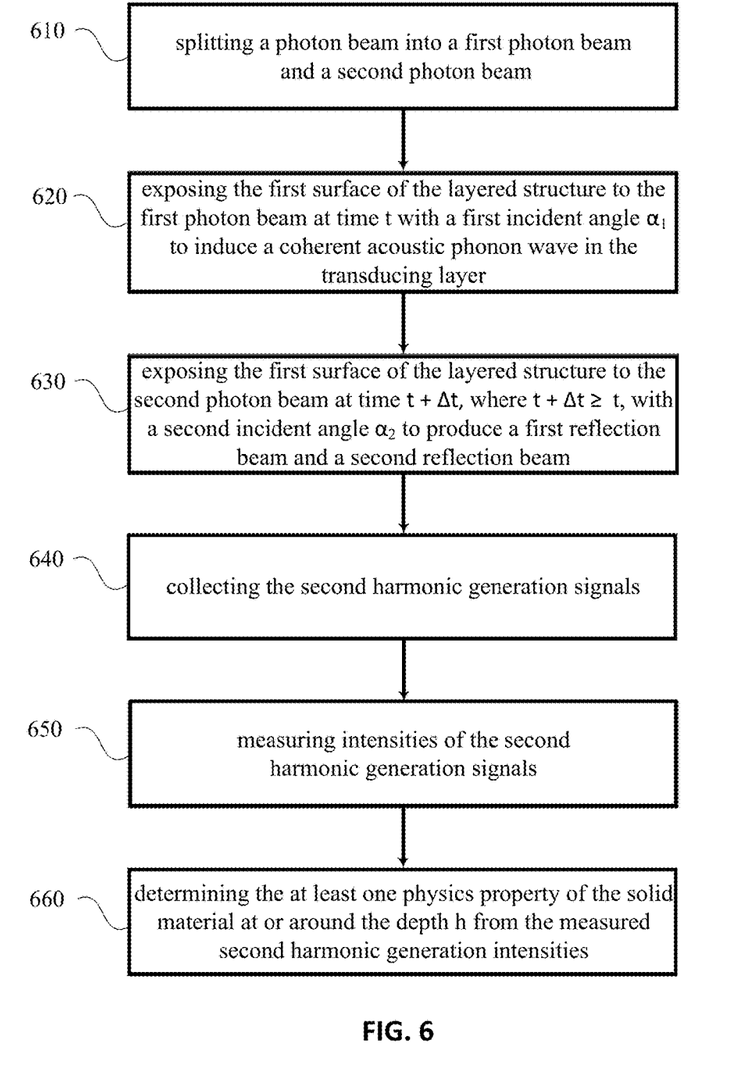
FIG. 6 shows a flowchart for non-invasively optical probing at least one physics property of a solid material according to one embodiment of the present invention.

Referring in general now to FIGS. 1-7, and in particular to FIGS. 1, 5 and 6, a method for non-invasively probing at least one physics property of a solid material, according to one embodiment of the present invention, is schematically illustrated. As shown in FIG. 5, a layered structure 550 is formed with a transducing layer 580 deposited on a solid material 590, where the solid material has a first surface 591, a second, opposite surface 593, and a body portion 590 therebetween the first surface 591 and the second surface 593. As formed, the layered structure 550 has a first surface 551 that is a surface (581) of the transducing layer 580, a second, opposite surface 553 that is a surface (593) of the solid material layer 590, and an interface 555 therebetween. The solid material layer 590 has at least one physics property same or different from that of the transducing layer 580.

The solid material layer 590 and the transducing layer 580 can be same or different materials. The solid material is one of a semiconductor material, a metallic material, an insulator material, and a dielectric material. The solid material is a target material with or without a layered structure. For examples, the solid material is one of GaAs, GaSb, GaSb/GaAs, Si, $SiO_2$/Si and silicon on insulator (SOI).

The transducing layer 580 is formed from one of a semiconductor material, a metallic material, an insulator material, and a dielectric material. For examples, the transducing layer is formed from one of GaAs, GaSb, GaSb/GaAs, Si, $SiO_2$/Si and silicon on insulator (SOI).

The interface 555 is one of a semiconductor/dielectric interface, a semiconductor/semiconductor interface, a metal/insulator interface, and a metal/dielectric interface, depending on what materials the solid material layer 590 and the transducing layer 580 are formed from.

In one embodiment of the present invention as shown in FIG. 5, the body portion of the solid material layer 590 has a thickness $H_2$, the transducing layer 580 has a thickness $H_1$, where the thickness $H_1$ and the thickness $H_2$ satisfying the relationship of $H_2/H_1 > 1$.

In another embodiment of the present invention, the transducing layer is formed from GaSb, the solid material is GaAs, the thickness $H_1$ is in the range of 10-30 nm, and the thickness $H_2$ is in the range of 50-1000 nm. In this particular exemplary embodiment, $H_2/H_1 \gg 1$ such that $H_2+H_1 \approx H_2$.

In one embodiment of the present invention, the target material can just be a solid material layer 590 with a thickness $H_2$.

As shown in FIGS. 1, 5 and 6, in one embodiment of the present invention, at step 610, a photon beam 102 is split into a first photon beam 104 (504), or a pump beam, and a second photon beam 106 (506), or a probe beam. The splitting can be done by utilizing a splitter.

At step 620, the first surface 551 of the layered structure 550 (150) is exposed to the first photon beam 504 (104) at time t with a first incident angle $\alpha_1$ to induce a coherent acoustic phonon wave in the transducing layer 580, which travels into the body portion of the solid material layer 590 with a moving surface that causes transient strain therein. The first incident angle $\alpha_1$ is the angle between the first photon beam 504 (104) and an axis perpendicular, e.g. axis Z as shown in FIG. 5, to the first surface 551 of the layered structure 550, and satisfies the relationship of: $0 \leq \alpha_1 < 90°$. In one embodiment of the present invention as illustrated in FIG. 1, the first incident angle $\alpha_1$ is $0°$.

At step 630, still referring to FIGS. 1, 5 and 6, the first surface 551 of the layered structure is exposed to the second photon beam 106 (506) at time $t+\Delta t$, where $t+\Delta t \geq t$, with a second incident angle $\alpha_2$ to produce a first reflection beam 154 and a second reflection beam 156, respectively. The time difference between the arriving times of the first photon beam and the second photon beam at the first surface of the layered structure, $\Delta t$, depends on the position of delay stage 108, which can be adjusted accordingly to adjust the time difference. The second incident angle $\alpha_2$ is the angle between the second photon beam 506 (106) and the axis perpendicular, e.g. axis Z as shown in FIG. 5, to the first surface 551 of the layered structure 550, and satisfies the relationship of: $0 < \alpha_2 < 90°$. In one embodiment of the present invention as illustrated in FIG. 1, the second incident angle $\alpha_2$ satisfies the relationship of: $\alpha_1(=0) < \alpha_2 < 90°$.

As such reflected, the first reflection beam has a first portion of the second photon beam that is reflected from the first surface 551 of the layered structure 550, and the second reflection beam has a second portion of the second photon beam that is reflected from the moving surface 551 of the coherent acoustic phonon wave traveling in the body portion of the solid material layer 590 at a depth h, causing an interference between the first reflection beam and the second reflection beam to generate corresponding second harmonic generation signals 156. The depth h can be counted from the first surface 551 of the layered structure 550 such that h satisfies the relationship of $0 \leq h \leq H_2 + H_1$. In this case, the corresponding second harmonic generation signals 156 can contain information related to physics properties of the transducing layer when $0 \leq h < H_1$, physics properties of the interface 591 when $h = H_1$, or physics properties of the solid material layer when $H_1 \leq h \leq H_2 + H_1$.

At step 640, after the reflected fundamental signals 154 and SHG signals 156 are separated by a dichroic beam splitter 162, the SHG signals are collected or detected by a photomultiplier tube such as a PMT 168.

The intensities of the SHG signals are measured with a photon counter 172 at step 650, and the at least one physics property of the solid material at or around the depth h is determined from the measured SHG intensities, respectively.

In one embodiment, the incident photon beam 102 includes a monochromatic, pulsed laser beam emitted from a 5 W Verdi pumped Mira Ti:sapphire laser (for example, a Mira 900, Coherent, Inc., Santa Clara, Calif.), at a wavelength set to 885 nm (about 1.5 eV) with average power of 600-730 mW. Other lasers, such as a free electron laser, can also be employed to practice the current invention. The transducing layer is formed from GaSb, the solid material is GaAs, the thickness $H_1$ is in the range of 10-30 nm, and the thickness $H_2$ is in the range of 50-1000 nm.

The at least one physics property of the solid material that is determinable from the measured SHG signals is one of defect, defect concentration, defect sensitivity, type of defect, spatial resolution, electronic structure, lattice, lattice mismatch, lattice disorder, dopants, impurities, interface(s), interfacial strain, interface roughness, interface state density, trapped charge density, surface recombination velocity, electrically active impurity, and interface morphology.

Figure 7:
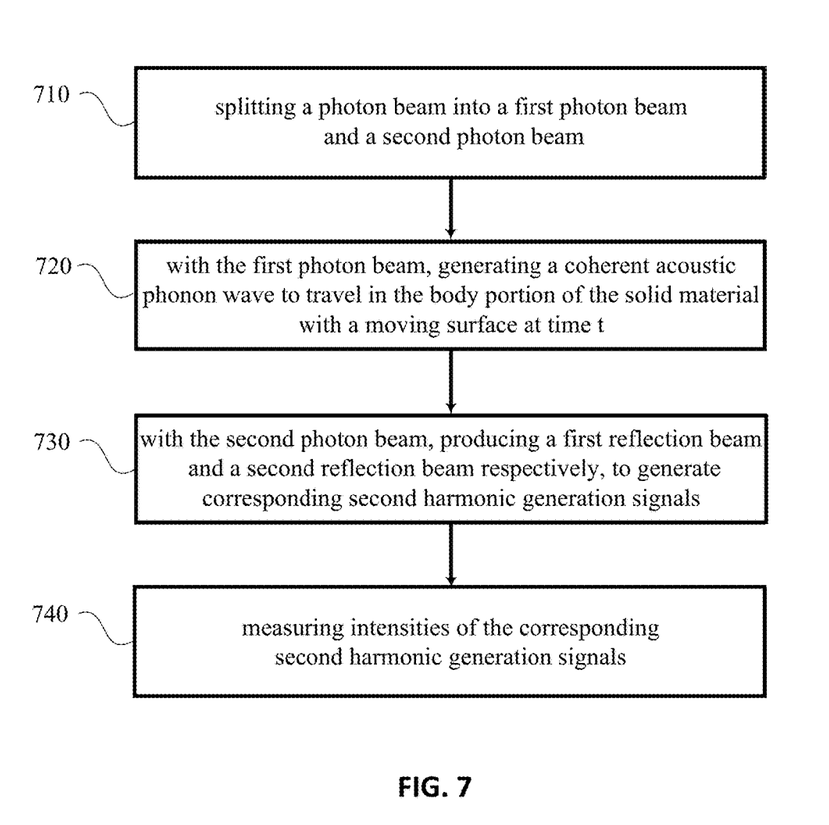
FIG. 7 shows a flowchart for non-invasively optical probing at least one physics property of a solid material according to another embodiment of the present invention.

Another aspect of the present invention relates to a method for non-invasively probing at least one physics property of a solid material. In one embodiment, referring now to FIGS. 1, 5 and 7, the solid material has a first surface 591, a second, opposite surface 593, and a body portion 590 therebetween the first surface 591 and the second surface 593. The method is practiced as follows:

At step 710, a photon beam 102 is split into a first photon beam 104 and a second photon beam 106.

At step 720, with the first photon beam, a coherent acoustic phonon wave is generated to travel in the body portion of the solid material with a moving surface at time t.

At step 730, with the second photon beam, a first reflection beam and a second reflection beam are produced, respectively, where the first reflection beam cotains a first portion of the second photon beam that is not reflected from the coherent acoustic phonon wave, and the second reflection beam contains a second portion of the second photon beam that is reflected, at a time t+Δt, where t+Δt≥t, from the moving surface of the coherent acoustic phonon wave traveling in the body portion of the solid material layer 590 at a depth h, causing an interference between the first reflection beam and the second reflection beam to generate corresponding second harmonic generation signals.

And at step 740, intensities of the corresponding second harmonic generation signals are measured, from which the at least one physics property of the solid material at or around the depth h is determinable.

The incident photon beam includes substantially monochromatic electromagnetic radiation. In one embodiment, the substantially monochromatic electromagnetic radiation is a laser beam such as a pulsed laser beam.

The solid material is one of a semiconductor material, a metallic material, an insulator material, and a dielectric material. For examples, the solid material is one of GaAs, GaSb, GaSb/GaAs, Si, $SiO_2$/Si and silicon on insulator (SOI).

Yet another aspect of the present invention relates to a non-invasive optical probe for at least one physics property of a solid material, where the solid material has a first surface 591, a second, opposite surface 593, and a body portion 590 therebetween the first surface 591 and the second surface 593. In one embodiment, the probe has a light source 101 for emitting a light beam 102, and optical means for splitting the light beam 102 into a first photon beam 104 to generate a coherent acoustic phonon wave to travel in the body portion of the solid material with a moving surface at time t, and a second photon beam 106 to produce a first reflection beam and a second reflection beam, respectively, where the first reflection beam contains a first portion of the second photon beam that is not reflected from the coherent acoustic phonon wave, and the second reflection beam contains a second portion of the second photon beam that is reflected, at a time t+Δt, where t+Δt≥t, from the moving surface 551 of the coherent acoustic phonon wave traveling in the body portion of the solid material layer 590 at a depth h, causing an interference between the first reflection beam and the second reflection beam to generate corresponding second harmonic generation signals. The probe also has a detector 172 for measuring intensities of the corresponding second harmonic generation signals, where the measured second harmonic generation signal intensities are associated with the at least one physics property of a solid material at or around the depth h.

In one embodiment, the light source is a laser.

In one embodiment, the optical means includes a splitter.

In one embodiment, the detector inlcudes a photomultiplier tube.

A further aspect of the present invention relates to a non-invasive optical probe for at least one physics property of a solid material, where the solid material has a first surface 591, a second, opposite surface 593, and a body portion 590 therebetween the first surface 591 and the second surface 593. In one embodiment, such a probe has a laser source 101 emitting a beam of pulses 102, where the beam of pulses 102 is split into a first photon beam 104 to generate a coherent acoustic phonon wave to travel in the body portion of the solid material with a moving surface at time t, and a second photon beam 106 to produce a first reflection beam and a second reflection beam, respectively, wherein the first reflection beam contains a first portion of the second photon beam that is not reflected from the coherent acoustic phonon wave, and the second reflection beam contains a second portion of the second photon beam that is reflected, at a time t+Δt, where t+Δt≥t, from the moving surface of the coherent acoustic phonon wave traveling in the body portion of the solid material 590 at a depth h, causing an interference between the first reflection beam and the second reflection beam to generate corresponding second harmonic generation signals. The probe also has an optical system for measuring intensities of the corresponding second harmonic generation signals, where the measured second harmonic generation signal intensities are associated with the at least one physics property of the solid material at or around the depth h.

The present invention further relates to a method for non-invasively probing at least one physics property of a solid material. In one embodiment, such a method has the steps of splitting a photon beam into a first photon beam and a second photon beam, exposing the solid material to the first photon beam to generate a coherent acoustic phonon wave in the solid material at time t, and exposing the solid material to the second photon beam at a time t+Δt, where t+Δt≥t, to generate corresponding second harmonic generation signals, where from the corresponding second harmonic generation signals, the at least one physics property of the solid material is determinable.

The present invention in another aspect relates to a non-invasive probe for at least one physics property of a solid material. In one embodiment, such a probe has a photon source emitting a beam of pulses, where the beam of pulses in operation is split into a first photon beam to generate a coherent acoustic phonon wave in the solid material at time t, and a second photon beam to generate corresponding second harmonic generation signals. The probe further has an optical system for measuring the corresponding second harmonic generation signals, where from the measured corresponding second harmonic generation signals, the at least one physics property of the solid material is determinable.

These and other aspects of the present invention are further described below.

Methods, Implementations and Examples of the Invention

Without intend to limit the scope of the invention, further exemplary procedures and preliminary experimental results of the same according to the embodiments of the present invention are given below.

As set forth above, coherent acoustic phonons (CAP) have been used for material characterization in the fields of picosecond acoustics, picosecond ultrasonics, and coherent acoustic phonon spectroscopy for some time. The acoustic pulse can result in a strain amplitude of up to $10^{-3}$ [10]. This strain amplitude is an order of magnitude higher than strain cited in the literature, which resulted in SHG enhancement due to modification of the $\chi^{(2)}$ tensor components [11]. The process for generating coherent acoustic phonons has been verified and well understood with ultrafast pump-probe technique [15, 16].

Figure 2A:
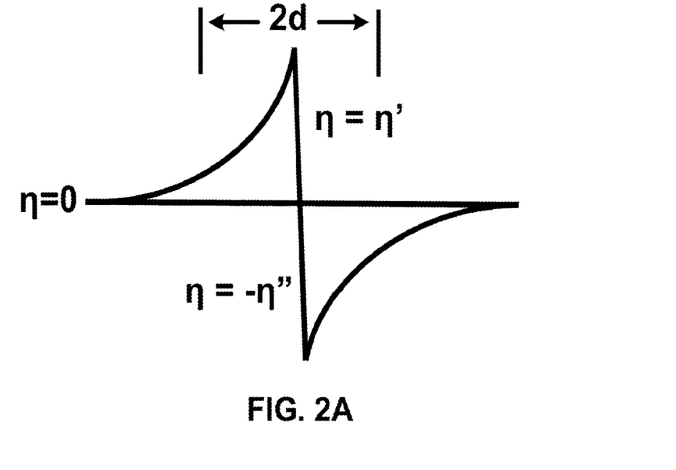
Figure 2B:
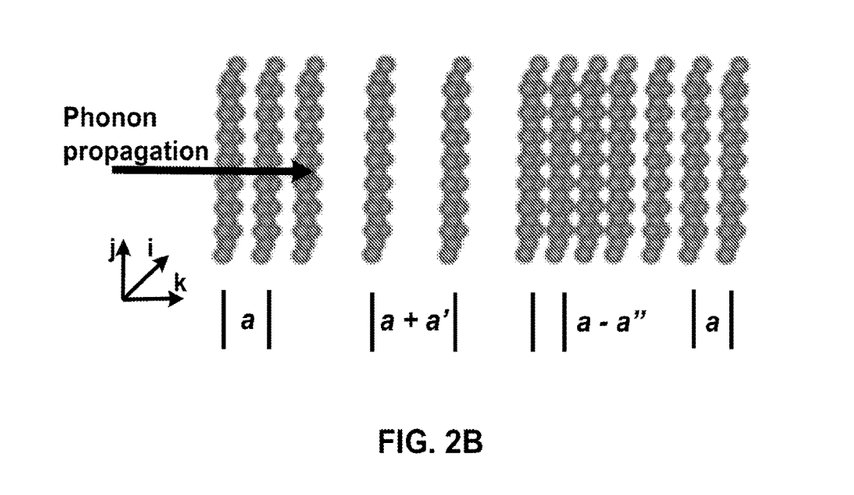

According to one embodiment of the present invention, a non-invasive optical probe 100 has a light source 101, an optical means and a detector 168, 172 and 174, as illustrated in part in FIG. 1. In this exemplary embodiment, the optical means includes a beam splitter 103 for splitting a laser beam 102 into a pump (first photon) beam 104 and a probe (second photon) beam 106. The optical means also includes a first set of optical components having two mirrors 105 and 107, a half-wave plate ($\lambda/2$) 111, a polarizer 112, a quarter-wave plate ($\lambda/4$) 113, an acousto-optic modulator (AOM) 114 and a lens 115 arranged in a first optical path as shown in FIG. 1 for delivering the pump beam 104 to the sample 150 at a time t. The optical means further includes a second set of optical components having a delay stage 108, a mirror 109, a half-wave plate ($\lambda/2$) 116, a polarizer 117 and a lens 118 arranged in a second optical path as shown in FIG. 1 for delivering the probe beam 106 to the sample 150 at a time t+$\Delta$t, where t+$\Delta$t≥t, to produce a reflection beam 152. In addition, the optical means also includes a dichroic beam splitter 162 arranged in a third optical path as shown in FIG. 1 for spatially separating the produced reflection beam 152 into a beam of the fundamental mode 154 and a beam of the second harmonic generation signals 156. In the embodiment, both of the pump beam 104 and the probe beam 106 have an identical wavelength that is the same as that of the laser beam 102. It should be noted that the wavelength of the second harmonic generation signals 156 is an half of that of the probe beam 106, while the wavelength of the fundamental mode 154 is the same as that of the probe beam 106. In this embodiment, the laser beam 102, which is generated from a laser source 101, is split by the beam splitter 103 into two beams 104, 106 with 50% as the pump beam 104 and 50% as the probe beam 106, respectively. When the pump beam pulse 104 with width ~10 μm and energy of ~1 nJ strikes the sample 150, which has a transducing layer 180 on a substrate 190, the 5-10 nm thick transducing layer 180 expands thermally. This expansion quickly generates an acoustic pulse tens of nanometers wide, which propagates through the sample 150 including the substrate 190 that is formed with target material. This acoustic pulse can have a strain amplitude up to $10^{-3}$. This strain amplitude is an order of magnitude higher than strain proven in the literature to contribute to SHG enhancement. FIG. 2 shows a theoretical shape of the pump beam, which shows spatial size in the order of thickness of the transducing layer, and a schematic cartoon illustration of crystal lattice modification by CAP wave according to one embodiment of the present invention. A probe beam 106 arrives sometime later at the sample, interacting with the strain wave. The probe power is increased to create second harmonic generation (SHG) in the target material of the substrate layer 190 (or the transducing layer 180) if it has an intrinsic $\chi^{(2)}$ or inherent broken centrosymmetry, a condition of SHG. In this way, the probe power monitors the change in $\chi^{(2)}$ or centrosymmetry caused by a coherent acoustic wave induced by the pump beam. These waves have produced a degree of SHG enhancement in preliminary measurements. The relative arrival time at the sample 150 between the two pulses 104, 106 depends on the position of the delay stage 108. By varying the optical delay line 108, one can track the optical reflectivity variation as a function of the position (depth h as illustrated in FIG. 5) of the acoustic strain into the material. A portion of the probe beam (e.g., probe beam 506 in FIG. 5) reflects off of the surface (e.g. surface 581 in FIG. 5) of the transducing layer (e.g., layer 580 in FIG. 5), and another portion of the probe beam (e.g., probe beam 506 in FIG. 5) reflects off of the traveling acoustic strain wave inside the substrate layer (layer 590) at depth h that is a variable. This causes the two probe beam linear reflections interfering destructively or constructively, producing oscillations in the optical reflectivity, which are typically detected and then collected in a detector (PD or PMT on both). In one embodiment of the present invention, two detection systems are utilized: photomultiplier 168 combined with a photon counter 172 to detect total SHG signal and photomultiplier 168 combined with a lock-in amplifier 174 working at the pump frequency to collect only the SHG signal generated by transient, dynamic strain (CAP pulse). From the detected SHG intensities by lock-in amplifier 174, one or more physics properties of the target material of the sample 150 at or around the depth h can be determined, e.g., at step 660 shown in FIG. 6.

When two photons of frequency ω are destroyed, a photon of frequency 2ω (second harmonic photon) is subsequently emitted. The measured second harmonic intensity from the material is expressed by:

$$I_{SHG} \propto |P^{(2)}(2\omega)|^2$$

where $P^{(2)}$ is the second order nonlinear polarizability. The second order nonlinear polarizability is described by:

$$P^{(2)} = \epsilon_0 \chi^{(2)} E^2$$

where $\epsilon_0$ is the permittivity of free space, $\chi^{(2)}$ is the second order nonlinear susceptibility tensor and E is electric field. In one embodiment of the present invention, measurements were taken at room temperature on a sample 150 with a GaAs substrate 190 with 20 nm GaSb transducing layer 180. The laser used to excite the sample was a Coherent Mira laser set to 885 nm, which is just below the band gap of GaAs (877 nm) to prevent carrier excitation in GaAs. The resulting, reflected probe beam 152 was sent through a dichroic beam splitter 162, transmitting the fundamental beam 154 to a static semiconductor detector 166 and reflecting the SHG beam into a PMT 168 (through Filter(s) 164). The delay stage 108 was fixed to particular relative arrival times to observe the change in SHG caused by a coherent acoustic pulse located at specific depths in the sample. The SHG spectra were observed at the following depths below the free surface 181 of sample 150: 200 nm, 400 nm, 600 nm and 800 nm. These were compared to the SHG response when there was no acoustic pulse (no pump spectrum in FIG. 3) and also when the CAP was created at the free surface (0 ps spectrum in FIG. 3). The responses of p-polarized pump, p-polarized probe and s-polarized SHG collection (PPS) and p-polarized pump, p-polarized probe and p-polarized SHG collection (PPP) are shown in FIG. 3, respectively.

The total enhancement of the SHG signal, shown in FIG. 3, is related to at least three contributions: point defects, lattice mismatch (in the case of multilayer structures) and transient strain caused by moving CAP. The areas in tension or compression (produced by CAP) change the lattice symmetry locally (see FIG. 2b). Owing to this technique, one is able to measure depth-dependent SHG created only by CAP wave with accuracy of tenths of nanometers. FIG. 4 presents changes of the separated second harmonic signal produced only by transient ultrafast pulse, dependent on azimuth angle according to one embodiment of the present invention. That means, one is able to follow any dynamic changes in the crystal symmetry with a nanometer-scale resolution. Information extracted from the measurements can be compared to a phenomenological model of SHG signal as well as by density functional theory (DFT) calculations.

The target materials for using this inventive technique or methodology to perform measurements are as follows: GaAs, GaSb/GaAs, Si, $SiO_2$/Si and silicon on insulator (SOI). The underlying physics of the CAP/SHG technique rely on the distortion of the material's local electronic structure through transient lattice strain caused by CAP. In areas of significant strain, the photoelastic constant is reduced, causing a change in the amount of probe light reflected at the traveling interface. This allows for measurement of any subsurface feature that induces strain, including intentional dopants, impurities, interfaces, interfacial strain arising from lattice mismatch and defect complexes. This CAP/SHG technique, which is the subject of this invention, has the potential to radically improve ability to identify and quantify order/disorder effect due to defects and transient strain at reduced cost and labor.

Numerous industrial applications can be explored and found. More specifically, the inventive technique or methodology as disclosed herein are utilizable in spatial resolution, defect sensitivity, determination of defect type, electronic structure effects:

(1) Spatial resolution—One of the primary aspects of materials characterization is how well and on what size scale features can be resolved. We intend to carry out a systematic study on both III-V materials (e.g. GaSb/GaAs) and $SiO_2$/Si structures. Currently, it is believed that the ultimate spatial resolution is on the order of twice the material's optical penetration depth (~10 nm).

(2) Sensitivity—The SHG technique is also extremely sensitive to various types of defect concentrations. Current experiments indicate that the technique is capable to measure electric fields as low as $10^3$ V/m, which is not achievable by the other techniques.

(3) Determination of disorder type—One of the most useful/powerful aspects of the combined CAP/SHG technique is its dependence on changes of crystal electric field and in consequence, strain tensor components of the material. As various crystal structure modifications (including crystal imperfections like dislocations, lattice mismatch, implanted dopants, etc.) have different SHG response at different depth. By repeating the CAP/SHG measurement as the time delay between pump and probe beam one is able to achieve the complete strain/dislocation depth profile of the target material.

(4) Electronic structure effects—Additionally, the reflection of the CAP probe light is primarily dependent on the local electronic structure surrounding the defects. This provides a convenient path to studying the complex interplay between defect strain and electronic structure distortion, including how many lattice points per defect are influenced.

Thus, according to one embodiment of the present invention, it is showed that CAP wave can allow one to accurately measure depth-dependent polar SHG profiles in a way not possible by any other technique. The above points provide a roadmap for making the technique a competitive characterization method, with great potential for industrial application.

In summary, this invention as set forth above provides a totally new approach to measure any strain, dopants, impurities, interfaces and interfacial strain arising from lattice deformation as a function of depth. This is a capability that is of great importance to the semiconductor device community as it provides a means of in-situ quality control.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1]. T. Saka et al. Y, *Strain of GaAs/GaAsP Superlattices Used as Spin-Polarized Electron Photocathodes, Determined by X-Ray Diffraction*, Surf. Sci. and Nanotech. 8 (2010) 125

[2]. X. Jin et al. *High-Performance Spin-Polarized Photocathodes Using a GaAs/GaAsP Strain-Compensated Superlattice*, Appl. Phys. Express 6 (2013) 015801

[3]. C. Schriever et al. *Strained silicon Photonics*, Materials 5 (2012) 889

[4]. Ji-Hong Zhao et al. *Enhancement of second-harmonic generation from silicon stripes under external cylindrical strain*, Opt. Lett. 34 (2009) 3340

[5]. M. M. Roberts et al. *Elastically relaxed free-standing strained-silicon nanomembranes*, Nature Mat. 5 (2006) 388

[6]. M. K. Vanbel et al. *Electric-Field-Induced Second-Harmonic Generation Demonstrates Different Interface Properties of Molecular Beam Epitaxy Grown MgO on Si*, J. Phys. Chem. C, 118 (2014) 1919

[7]. W. F. Smith, *Foundations of Materials Science and Engineering*, III-rd ed., McGraw-Hill, 2004

[8]. O. Matsuda, O. B. Wright, *Generation and Observation of GHz-THz Acoustic Waves in Thin Films and Microstructures Using Optical Methods*, Frontiers in Optical Methods 180 (2014) 129

[9]. I. L. Lyubchanskii et al. *Second-harmonic generation from realistic film-substrate interfaces: The effects of strain*, Appl. Phys. Lett. 76 (2000) 1848

[10]. C. Thomsen et al., *Surface Generation and Detection of Phonons by Picosecond Light Pulses*, Phys. Rev. B 34 (1986) 4129

[11]. Yu. D. Glinka et al. *Ultrafast dynamics of interfacial electric fields in semiconductor hetero-structures monitored by pump-probe second-harmonic generation*, Appl. Phys. Lett. 81 (2002) 3717

[12]. H. Park, et al. Applied Physics Letters 95 (2009) 062102

[13]. H. Park et al. *Polarization-dependent temporal behavior of second harmonic generation in $Si/SiO_2$ systems*, J. Opt. 13 (2011) 055202

[14]. K. S. Ni, H. Krzyzanowska, Y. Fu, P. M. Fauchet, *Lateral carrier Injection Infrared Light Emmitting Diode, Structure, Method and Application* US patent 2014/0027808

[15]. C. Thomsen et al., *Coherent Phonon Generation and Detection by Picosecond Light Pulses*, Phys. Rev. Lett. 53 (1984) 989

[16]. O. Matsuda et al. *Coherent shear phonon generation and detection with picosecond laser acoustics*, Phys. Rev. B 77 (2008) 224110

What is claimed is:

1. A method for non-invasively probing at least one physics property of a solid material, wherein the solid material is in a form of a solid material layer having a first surface, a second, opposite surface, and a body portion therebetween the first surface and the second surface, wherein a layered structure is formed with a transducing layer deposited on the solid material layer, and wherein as formed, the layered structure has a first surface that is a surface of the transducing layer, a second, opposite surface that is a surface of the solid material layer, and an interface therebetween, comprising the steps of:
    (a) splitting a photon beam into a first photon beam and a second photon beam, wherein both of the first photon beam and the second photon beam have an identical wavelength that is same as that of the photon beam;
    (b) exposing the first surface of the layered structure to the first photon beam at time t with a first incident angle $\alpha_1$ to induce a coherent acoustic phonon wave in the transducing layer, which travels into the body portion of the solid material layer with a moving surface;
    (c) exposing the first surface of the layered structure to the second photon beam at time $t+\Delta t$, where $t+\Delta t \geq t$, with a second incident angle $\alpha_2$ to produce a reflection beam comprising a first reflection beam and a second reflection beam, respectively, such that the first reflection beam comprises a first portion of the second photon beam that is reflected from the first surface of the layered structure, and the second reflection beam comprises a second portion of the second photon beam that is reflected from the moving surface of the coherent acoustic phonon wave traveling in the body portion of the solid material layer at a depth h, thereby causing an interference between the first reflection beam and the second reflection beam to generate corresponding second harmonic generation signals, wherein the second harmonic generation signals have a wavelength that is an half of the wavelength of the second photon beam;
    (d) spatially separating the produced reflection beam into a beam of the fundamental mode and a beam of the second harmonic generation signals, wherein the beam of the fundamental mode has a wavelength that is same as that of the second photon beam;
    (e) detecting the second harmonic generation signals;
    (f) measuring intensities of the second harmonic generation signals; and
    (g) determining the at least one physics property of the solid material at or around the depth h from the measured second harmonic generation intensities.

2. The method of claim 1, wherein the photon beam comprises substantially monochromatic electromagnetic radiation.

3. The method of claim 2, wherein the substantially monochromatic electromagnetic radiation comprises a laser beam.

4. The method of claim 3, wherein the laser beam comprises a pulsed laser beam.

5. The method of claim 1, wherein the solid material layer has at least one physics property same or different from that of the transducing layer.

6. The method of claim 1, wherein the body portion of the solid material layer has a thickness $H_2$.

7. The method of claim 6, wherein the solid material is one of a semiconductor material, a metallic material, an insulator material, and a dielectric material.

8. The method of claim 6, wherein the solid material is one of GaAs, GaSb, GaSb/GaAs, Si, $SiO_2$/Si and silicon on insulator (SOI).

9. The method of claim 6, wherein the transducing layer has a thickness $H_1$.

10. The method of claim 9, wherein the thickness $H_1$ and the thickness $H_2$ satisfying the relationship of $H_2/H_1 > 1$.

11. The method of claim 10, wherein the transducing layer is formed from GaSb, the solid material is GaAs, the thickness $H_1$ is in the range of 10-30 nm, and the thickness $H_2$ is in the range of 50-1000 nm.

12. The method of claim 1, wherein the transducing layer is formed from one of a semiconductor material, a metallic material, an insulator material, and a dielectric material.

13. The method of claim 12, wherein the transducing layer is formed from one of GaAs, GaSb, GaSb/GaAs, Si, $SiO_2$/Si and silicon on insulator (SOI).

14. The method of claim 1, wherein the interface is one of a semiconductor/dielectric interface, a semiconductor/semiconductor interface, a metal/insulator interface, and a metal/dielectric interface.

15. The method of claim 1, wherein the first incident angle $\alpha_1$ is the angle between the first photon beam and an axis perpendicular to the first surface of the layered structure, and satisfies the relationship of: $0 \leq \alpha_1 < 90°$.

16. The method of claim 15, wherein the second incident angle $\alpha_2$ is the angle between the second photon beam and the axis perpendicular to the first surface of the layered structure, and satisfies the relationship of: $0 < \alpha_2 < 90°$.

17. The method of claim 1, wherein the measuring step comprises the step of detecting the second harmonic generation signals by a photomultiplier tube.

18. The method of claim 17, wherein the measuring step is performed with a photon counter.

19. The method of claim 1, wherein the at least one physics property of the solid material comprises at least one of defect, defect concentration, defect sensitivity, type of defect, spatial resolution, electronic structure, lattice, lattice mismatch, lattice disorder, dopants, impurities, interface(s), interfacial strain, interface roughness, interface state density, trapped charge density, surface recombination velocity, electrically active impurity, and interface morphology.

20. A method for non-invasively probing at least one physics property of a solid material, wherein the solid material is in a form of a solid material layer having a first surface, a second, opposite surface, and a body portion therebetween the first surface and the second surface, comprising the steps of:
(a) splitting a photon beam into a first photon beam and a second photon beam, wherein both of the first photon beam and the second photon beam have an identical wavelength that is same as that of the photon beam;
(b) with the first photon beam, generating a coherent acoustic phonon wave to travel in the body portion of the solid material with a moving surface at time t;
(c) with the second photon beam, producing a reflection beam comprising a first reflection beam and a second reflection beam, respectively, such that the first reflection beam comprises a first portion of the second photon beam that is not reflected from the coherent acoustic phonon wave, and the second reflection beam comprises a second portion of the second photon beam that is reflected, at a time t+Δt, where t+Δt≥t, from the moving surface of the coherent acoustic phonon wave traveling in the body portion of the solid material layer at a depth h, thereby causing an interference between the first reflection beam and the second reflection beam to generate corresponding second harmonic generation signals, wherein the second harmonic generation signals have a wavelength that is an half of the wavelength of the second photon beam;
(d) spatially separating the produced reflection beam into a beam of the fundamental mode and a beam of the second harmonic generation signals, wherein the beam of the fundamental mode has a wavelength that is same as that of the second photon beam; and
(e) measuring intensities of the corresponding second harmonic generation signals, from which the at least one physics property of the solid material at or around the depth h is determinable.

21. The method of claim 20, wherein the photon beam comprises substantially monochromatic electromagnetic radiation.

22. The method of claim 21, wherein the substantially monochromatic electromagnetic radiation comprises a laser beam.

23. The method of claim 22, wherein the laser beam comprises a pulsed laser beam.

24. The method of claim 20, wherein the solid material is one of a semiconductor material, a metallic material, an insulator material, and a dielectric material.

25. The method of claim 24, wherein the solid material is one of GaAs, GaSb, GaSb/GaAs, Si, $SiO_2$/Si and silicon on insulator (SOI).

26. The method of claim 20, wherein the measuring step comprises the step of detecting the corresponding second harmonic generation signals by a photomultiplier tube.

27. The method of claim 26, wherein the measuring step is performed with a photon counter.

28. The method of claim 20, wherein the at least one property of the solid material comprises at least one of defect, defect concentration, defect sensitivity, type of defect, spatial resolution, electronic structure, lattice, lattice mismatch, lattice disorder, dopants, impurities, interface(s), interfacial strain, interface roughness, interface state density, trapped charge density, surface recombination velocity, electrically active impurity, and interface morphology.

29. A non-invasive optical probe for probing at least one physics property of a solid material, wherein the solid material is in a form of a solid material layer having a first surface, a second, opposite surface, and a body portion therebetween the first surface and the second surface, comprising:
(a) a light source for emitting a light beam;
(b) optical means for
splitting the light beam into a first photon beam and a second photon beam wherein both of the first photon beam and the second photon beam have an identical wavelength that is same as that of the light beam;
delivering the first photon beam to the solid material to generate a coherent acoustic phonon wave to travel in the body portion of the solid material with a moving surface at time t;
delivering the second photon beam to the solid material to produce a reflection beam comprising a first reflection beam and a second reflection beam respectively, such that the first reflection beam comprises a first portion of the second photon beam that is not reflected from the coherent acoustic phonon wave, and the second reflection beam comprises a second portion of the second photon beam that is reflected, at a time t+Δt, where t+Δt≥t, from the moving surface of the coherent acoustic phonon wave traveling in the body portion of the solid material layer at a depth h, thereby causing an interference between the first reflection beam and the second reflection beam to generate corresponding second harmonic generation signals, wherein the second harmonic generation signals have a wavelength that is an half of the wavelength of the second photon beam;
spatially separating the produced reflection beam into a beam of the fundamental mode and a beam of the second harmonic generation signals, wherein the beam of the fundamental mode has a wavelength that is same as that of the second photon beam; and
(c) a detector for measuring intensities of the corresponding second harmonic generation signals,
wherein the measured second harmonic generation signal intensities are associated with the at least one physics property of a solid material at or around the depth h.

30. The non-invasive optical probe of claim 29, wherein the light source comprises a laser.

31. The non-invasive optical probe of claim 29, wherein the solid material is one of a semiconductor material, a metallic material, an insulator material, and a dielectric material.

32. The non-invasive optical probe of claim 29, wherein the solid material is one of GaAs, GaSb, GaSb/GaAs, Si, $SiO_2$/Si and silicon on insulator (SOI).

33. The non-invasive optical probe of claim 29, wherein the optical means comprises:
a splitter for splitting the light beam into the first light beam and the second light beam;
a first set of optical components arranged in a first optical path for delivering the first light beam to the solid material at a time t;
a second set of optical components arranged in a second optical path for delivering the second light beam to the solid material at a time t+Δt to produce the reflection beam; and
a dichroic beam splitter arranged in a third optical path for spatially separating the produced reflection beam into the beam of the fundamental mode and the beam of the second harmonic generation signals.

34. The non-invasive optical probe of claim 29, wherein the detector comprises a photomultiplier tube.

35. A non-invasive optical probe for probing at least one physics property of a solid material, wherein the solid material has a first surface, a second, opposite surface, and a body portion therebetween the first surface and the second surface, comprising:
   (a) a laser source emitting a beam of pulses; and
   (b) an optical system configured to:
      split the beam of pulses into a first photon beam and a second photon beam, wherein both of the first photon beam and the second photon beam have an identical wavelength that is same as that of the beam of pulses;
      deliver the first photon beam to the solid material to generate a coherent acoustic phonon wave to travel in the body portion of the solid material with a moving surface at time t;
      deliver the second photon beam to the solid material to produce a reflection beam comprising a first reflection beam and a second reflection beam at a time $t+\Delta t$, where $t+\Delta t \geq t$, such that the first reflection beam comprises a first portion of the second photon beam that is not reflected from the coherent acoustic phonon wave, and the second reflection beam comprises a second portion of the second photon beam that is reflected from the moving surface of the coherent acoustic phonon wave traveling in the body portion of the solid material at a depth h, thereby causing an interference between the first reflection beam and the second reflection beam to generate corresponding second harmonic generation signals, wherein the second harmonic generation signals have a wavelength that is an half of the wavelength of the second photon beam;
      spatially separate the produced reflection beam into a beam of the fundamental mode and a beam of the second harmonic generation signals, wherein the beam of the fundamental mode has a wavelength that is same as that of the second photon beam; and
      measure intensities of the corresponding second harmonic generation signals,
   wherein the measured second harmonic generation signal intensities are associated with the at least one physics property of the solid material at or around the depth h.

36. The non-invasive optical probe of claim 35, wherein the solid material is one of a semiconductor material, a metallic material, an insulator material, and a dielectric material.

37. The non-invasive optical probe of claim 35, wherein the solid material is one of GaAs, GaSb, GaSb/GaAs, Si, $SiO_2$/Si and silicon on insulator (SOI).

* * * * *